United States Patent [19]

Magda et al.

[11] Patent Number: 5,714,328
[45] Date of Patent: Feb. 3, 1998

[54] RNA PHOTOCLEAVAGE USING TEXAPHYRINS

[75] Inventors: Darren Magda, Cupertino, Calif.; Jonathan L. Sessler, Austin, Tex.

[73] Assignees: Board of Regents, the University of Texas System, Austin, Tex.; Pharmacyclics, Inc., Sunnyvale, Calif.

[21] Appl. No.: 484,551

[22] Filed: Jun. 7, 1995

[51] Int. Cl.[6] .............................. C12Q 1/65; C12Q 1/70; C07H 21/04; A61K 48/00
[52] U.S. Cl. ............................... 435/6; 435/5; 536/24.5; 514/44; 514/2; 424/9.362
[58] Field of Search ..................... 435/6, 5; 536/24.5; 514/44, 2; 424/9.362; 204/157.5; 604/4, 5

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,135,717 | 8/1992 | Renzoni et al. | 422/61 |
| 5,141,911 | 8/1992 | Meunier et al. | 502/159 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | |

FOREIGN PATENT DOCUMENTS

| | | |
|---|---|---|
| 0111418 | 6/1984 | European Pat. Off. |
| 0196515 | 10/1986 | European Pat. Off. |
| 0214908 A1 | 3/1987 | European Pat. Off. |
| 0233701 A2 | 8/1987 | European Pat. Off. |
| 2697254 | 4/1994 | France |
| WO 90/02747 | 3/1990 | WIPO |
| 90/01208 | 8/1990 | WIPO |
| WO 90/10633 | 9/1990 | WIPO |
| 91/19730 | 12/1991 | WIPO |
| 92/01781 | 2/1992 | WIPO |
| WO 93/14093 | 7/1993 | WIPO |
| WO 94/09003 | 4/1994 | WIPO |
| WO 94/29316 | 12/1994 | WIPO |
| WO 95/21845 | 8/1995 | WIPO |
| WO 95/29702 | 11/1995 | WIPO |
| WO 96/07667 | 3/1996 | WIPO |
| WO 96/09315 | 3/1996 | WIPO |

OTHER PUBLICATIONS

Magda, et al., "Texaphyrin–based nuclease analogs. Rationally designed approaches to the catalytic cleavage of RNA and DNA targets," *Chemical Abstracts* 125(7):5032 (Aug. 1996).

International Search Report for related foreign application PCT/US96/09419, date of mailing Dec. 17, 1996.

International Search Report mailed Feb. 9, 1996.

Casas et al., "Preparation of Hybrid DNA Cleaver–Oligonucleotide Molecules Based on a Metallotris (methylpyridiniumyl) porphyrin Motif," *Bioconjugate Chem.*, vol. 4, No. 5, pp. 366–371, Sep./Oct. 1993.

Monsigny, M., et al., "Glycoconjugates as Carriers for Specific Delivery of Therapeutic Drugs and Genes," *Adv. Drug Deliv. Rev.* (Netherlands), 14/1:1–24, 1994. Abstract only.

Gura, Science 270: 575–577 (1995).

James, Antiviral Chemistry and Chemotherapy 2(4) 191–214 (1991).

Iverson et al. Pure and Applied Chem 66:845–850 (1994).

Mastruzzo et al. Photochemistry and Photobiology 60:316–322 (1994).

Mestre et al. Bioconjugate Chemistry 6 (4) 466–472 (1995).

Abid et al., "Lanthanide Complexes of Some Macrocyclic Schiff Bases Derived from Pyridine–2, 6–dicarboxaldehyde and $\alpha$, $\omega$–Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrole Macrocycle", *Tetrahedron Lett.*, 25:3269–3270, 1984.

Ansell, "X–Ray Crystal Structure of the Pentagonal Bipyramidal Nickel(11) Complex $[Ni^{11}(L) (H_2O)_2] (BF_4)_2$ and the Selective Stabilisation of the Nickel(1) Oxidation State by a Quinquedentate Macrocyclic Ligand", *J. Chem. Soc., Chem. Commun.* 10: pp. 546–547, 1982.

(List continued on next page.)

*Primary Examiner*—W. Gary Jones
*Assistant Examiner*—Dianne Rees
*Attorney, Agent, or Firm*—Akin, Gump, Strauss, Hauer & Feld, L.L.P.

[57] ABSTRACT

Methods for photocleavage of a polymer of ribonucleic acid using a texaphyrin or a texaphyrin metal complex are provided. A preferred method of use is the site-specific cleavage of a polymer of ribonucleic acid and a preferred texaphyrin is a derivatized texaphyrin having binding specificity, in particular, a texaphyrin covalently coupled to a site-directing molecule, preferably an oligonucleotide. Possible substrates for cleavage include messenger, ribosomal, transfer, small nuclear, and small cytosolic ribonucleic acids, and RNA cofactors, thereby inactivating these ribonucleic acids and providing a multifaceted approach for treating benign or malignant cancer cells, or other undesired cells or tissues.

15 Claims, 5 Drawing Sheets

OTHER PUBLICATIONS

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur-containing Polypyrrolic Macrocycles. Sulphur Extrusion from a meso-Thiaphlorin", *J. Chem. Soc., Chem. Commun.* vol 197: pp. 807–809, 1970.

Broadhurst et al., "18-and 22-π-Electron Macrocycles Containing Furan, Pyrrole, and Thiophen Rings", *J. Chem. Soc., Chem. Commun.* 1:pp. 1480–1482, 1969.

Broadhurst et al., "New Macrocyclic Aromatic Systems Related to Porphins", *J. Chem. Soc., Chem. Commun.* 1624:pp. 23–24, 1969.

Broadhurst et al., "The Synthesis of 22 π–Electron Macrocycles. Sapphyrins and Related Compounds", *J. Chem. Soc. Perkin Trans.*, 1:2111–2116, 1972.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97:4519–4527, 1975.

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew. Chem., Int. Ed Engl.*, 25:1100–1101, (1986).

Gossauer, "Syntheses of Some Unusual Polypyrrole Macrocycles", *Bull. Soc. Chim. Belg.*, 92:793–795, (1983).

Knubel et al., "Biomimetic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 π–Electron Tetrapyrrolic Annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 π–Electron Macrocycle: Pentaphyrin", *J. Chem. Soc., Chem. Commun.*, 20:p. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Tweedle et al., "Principles of Contrast–Enhanced MRI", in Magnetic Resonance Imaging, 2nd ed. Partain, et al. Eds., W. B. Saunders: Philadelphia, vol. I (1988) 793–809.

Vogel et al., "Porphycene –a Novel Porphin Isomer", *Angew. Chem., Int. Ed. Engl.*, 25:257–259, 1986.

Vogel et al., "2,7,12,17-Tetrapropylporphycene –Counterpart of Octaethylporphyrin in the Porphycene Series", *Angew. Chem., Int. Ed. Engl.*, 26:928–931, 1987.

Sessler et al., "A Water–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 5:314–316, 1989. Submitted as A32 in 1449 for UTSB:458.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988. No vol. No. applicable.

Sessler et al., "Tripyrroledimethine–derived (Texaphyrin-type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin': A Novel 22 π–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

Sessler et al., "Synthesis and Structural Characterixation of Lanthanide(III) Texaphyrins." *Inorganic Chemistry*, 32(14):3175–3187, 1993.

"2–Äthylamino–2–methyl–propanol–(1)", *Beilstein's Handbuch*, 4:785, 1950.

"Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, 1992, Washington, DC.

Sessler, Jonathan L., "Texas–Sized Molecule." *Discovery*, 13(1):44–49, 1993.

Sessler et al., "Photodynamic Inactivation of Enveloped Viruses Using Sapphyrin, α 22 π–Electron Expanded Porphyrin: Possible Approaches to Prophylactic Blood Purification Protocols," *SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son-of-Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. Am. Chem. Soc.*, 1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine–and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalcator Group, and a Catalytic Site," *J. Chem. Soc. Chem. Commum.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Kimura, "Macrocyclic Polyamines as Biological Cation and Anion Complexones –An Application to Calculi Dissolution," 113–141.

Li and Diederich, "Carriers for Liquid Membrane Transport of Nucleotide 5'–Triphosphates," *J. Org. Chem.*, 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato)uranium(VI) and Its Derivatives," *J. Am. Chem. Soc.*, 1978, 1695–1705. vol. 100: 1695–1705, 1978.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases –Superiority of Macrobicyclid Host Molecules," *Angew, Chem. Int. Ed. Engl.*, 1991, 30(4):442–444.

Sessler et al., "Anion Binding: A New Direction in Prophyrin–Related Research," *Pure & Applied Chem.*, 65(3):393–398, 1993.

Sessler et al., "Cytosine Amine Derivatives," *J. Org. Chem.*, 1992, 47:826–834.

Aoyama et al., "Multi–Point Interaction of Phosphates with Protonated Pyridylporphyrin. Discrimination of Monoalkyl and Dialkyl Phosphates," *Chemistry Letters*, 7:1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

Nam–Chiang Wang et al., "Pyrrole chemistry. XVII. Alkylation of the pyrrolyl ambident anion," *Can. J. Chem.*, 55:4112–4116, 1977.

T.D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (III) Texaphyrin: A Novel MRI Contrast Agent," *Journal of the American Chemical Society*, 115(22):10,368–10,369,1993.

Iverson et al., "Interactions Between Expanded Porphyrins and Nucleic Acids," *Pure Applied Chemistry*, 66(4):845–850, 1994.

Matthews et al., "Inactivation of Viruses with Photoactive Compounds," *Blood Cells*, 18(1):75–89, 1992.

Ehrenberg et al., "Spectroscopy, Photokinetics and Cellular Effect of Far–Red and Near Infrared Absorbing Photosensitizers," *Proc. SPIE–Int. Soc. Opt. Eng 1992*, vol. 1645, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993. (vol. No. not applicable).

Lin et al., "use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA•Fe(II)," *Proc. Natl. Acad. Sci. USA*, 82:968–972, 1985.

Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Doan et al., "Targeted Cleavage of Polynucleotides by Complementary Oligonucleotides Covalently Linked to Iron–Porphyrins," *Biochemistry*, 26:6736–6739, 1986.

Dervan, Peter B., "Design of Sequence–Specific DNA–Binding Molecules," *Science*, 232:464–471, 1986.

Groves and Farrell, "DNA Cleavage by a Metal Chelating Tricationic Porphyrin," *J. Am. Chem. Soc.*, 111:4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucleotide Derivatives for Sequence Specific Chemical Modification and Cleavage of DNA," *Nucleosides & Nucleotides*, 10(1–3):641–643, 1991.

Zuk et al., "Pharmacokinetic and Tissue Distribution Studies of the Photosensitizer bis(Di–Isobutyl Octadecysiloxy)Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fullerene–Oligonucleotide Conjugates: Photo–Induced Sequence Specific DNA Cleavage", *Agnew. Chem. Int. Ed. Engl.*, 33(23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem, Photobiol.*, 60(4):316–322, 1994.

Fedorova et al., "Palladium(II)–Coproporphyrin I as a Photoactivable Group in Sequence–Specific Modification of Nucleic Acids by Oligonucleotide Derivatives," *FEBS Lett.*, 259(2):335–337, 1990.

Morgan and Skalkos, "Second Generation Sensitizers: Where are We and Where Should We Be Going?" *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.*, 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*, 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA*, 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OEPc and EtioPc)–Tetra–and Pentacoordinated Zinc Complexes of OEPc," *Angew. Chem. Int. Ed. Engl.*, 32(11):1600–1604, 1993.

Wessel et al., "Porphyrins with Aromatic 26π–Electron Systems," *Agnew. Chem. Int. Ed. Eng.*, 32(8):1148–1151, 1993.

Agrawal et al., "Cellular Uptake and Anti–HIV Activity of Oligonucleotides and Their Analogs," *Gene Regulation: Biology of Antisense RNA and DNA*, 273–283, 1992. No vol. no applicable.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992. No vol. # applicable.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992. No vol. # applicable.

Breslow et al., "Effects of Metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in the Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resultinhg in a Binuclear Co(III) Complex with a Novel Doubly Bidentate $\mu^4$-Phosphato Bridge," *J. Am. Chem. Soc.*, 111:4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992. No vol. # applicable.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 8:640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with (Lys)$_2$Cu as the Core Motif," *Journal of the Chemical Society*, 4:337–339, 1993.

Sessler et al., "Sapphyrins: New Life for an Old Expanded Porphyrin," *Synlett*, 3:127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'–= Cyclic Adenosine Monophosphate by Cerium((III) Hydroxide Cluster," *J. Chem. Soc. Chem. Comm.*, 23: pp. 1707–1708, 1992.

To and Neiman, "The Potential for Effective Antisense Inhibition of Retroviral Replication Mediated by Retroviral Vectors," *Gene Regulation: Biology of Antisense RNA and DNA*, 261–271, 1992. No vol. # applicable.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site–Selective Hydrolysis of tRNA by Lanthanide Metal Complexes," *Inorg. Chem.*, 32:5899–5900, 1993.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic Anionic, and Neutral Substrates, in Transition Metals in Supramolecular Chemistry," L. Fabbrizzi and A. Poggi, Editors, NATO ASI Series, Kluwer, Amsterdam, pp. 391–408, 1994.

PCT Search Report mailed Feb. 23, 1995.

International Search Report mailed Dec. 6, 19994.

International Search Report Mailed Feb.22, 1994.

International Search Report mailed Feb. 3, 1994.

U.S. Serial No. 08/075,123 to Sessler et al. filed Jun. 9, 1993.

U.S. Serial No. 08/098,514 to Sessler et al. filed Jul. 28, 1993.

U.S. Serial No. 08/112,786 to Sessler et al. filed Aug. 25, 1993.

U.S. Serial No. 08/135,118 to Sessler et al. filed Oct. 12, 1993.

U.S. Serial No. 08/302,061 to Sessler et al. filed Sep. 7, 1994.

U.S. Serial No. 08/280,351 to Sessler et al. filed Jul. 26, 1994.

U.S. Serial No. 08/196,964 to Sessler et al. filed Feb. 15, 1994.

U.S. Serial No. 227,370 to Sessler et al. filed Apr. 14, 1994.

U.S. Serial No. 08/207,845 to Sessler et al. filed Mar. 8, 1994.

U.S. Serial No. 08/452,261 to Sessler et al. filed May 26, 1995.

U.S. Serial No. 08/236,218 to Sessler et al. filed Apr. 28, 1994.

U.S. Serial No. 08/310,501 to Sessler et al. filed Sep. 21, 1994.

U.S. Serial No. 08/437,968 to Sessler et al. filed May 10, 1995.

U.S. Serial No. 08/433,573 to Sessler et al. filed May 3, 1995.

U.S. Serial No. 8/449,417 to Sessler et al. filed May 24, 1995.

U.S. Serial No. 08/458,909 to sessler et al. filed Jun. 2, 1995.

U.S. Serial No. 08/449,681 to Sessler et al. filed May 24, 1995.

U.S. Serial No. 08/484,557 to Sessler et al. filed Jun. 7, 1995.

U.S. Serial No. 08/458,347 to Sessler et al. filed Jun. 2, 1995.

U.S. Serial No. 08/459,333 to Sessler et al. filed Jun. 2, 1995.

U.S. Serial No. 08/485,581 to Magda et al. filed Jun. 7, 1995.

U.S. Serial No. 08/486,962 to Magda et al. filed Jun. 7, 1995.

U.S. Serial No. 08/486,886 to Hemmi et al. filed Jun. 7, 1995.

U.S. Serial No. 08/486,935 to Hemmi et al. filed Jun. 6, 1995.

U.S. Serial No. 08/486,209 to Hemmi et al. filed Jun. 6, 1995.

U.S. Serial No. 08/469,177 to Magda et al. filed Jun. 6, 1995.

U.S. Serial No. 08/486,967 to Sessler et al. filed Jun. 7, 1995.

U.S. Serial No. 08/486,311 to Magda et al. filed Jun. 7, 1995.

U.S. Serial No. 08/487,722 to Magda et al. filed Jun. 7, 1995.

RNA PHOTOCLEAVAGE USING TEXAPHYRINS

BACKGROUND OF THE INVENTION

Photodynamic therapy (PDT) is a treatment technique that uses a photosensitizing dye, which localizes at, or near, the treatment site, and when irradiated in the presence of oxygen serves to produce cytotoxic materials, such as singlet oxygen ($O_2(^1\Delta_g)$) from benign precursors (e.g. ($O_2(^3\Sigma_g-)$). Other reactive species such as superoxide, hydroperoxyl, or hydroxyl radicals may be involved. At the doses used, neither the light nor the drug has any independent biological effect. In PDT, the photosensitizer acts in a catalytic' way, since its function is not to react directly with the cellular targets, but to absorb light energy and to transfer it to molecular oxygen, regenerating ground state photosensitizer.

The effectiveness of PDT is predicated on three additional factors: i) The photosensitive dyes used in PDT must have the ability to localize at the treatment site as opposed to surrounding tissue. ii) The high reactivity and short lifetime of activated oxygen means that it has a very short range and is unlikely to escape from the cell in which it is produced; cytotoxicity is therefore restricted to the precise region of tissue absorbing light, perhaps down to the cellular level. iii) Developments in lasers and fiber optics allow a beam of intense light to be delivered precisely to many parts of the body.

For reviews of photodynamic therapy, see U.S. Pat. No. 5,252,720 (incorporated by reference herein); Sindelar et al., (1991); Grossweiner, L. I., (1991); Henderson, B. W. and T. J. Dougherty, (1992); and Moan, J. and K. Berg, (1992). In recent years, considerable effort has been devoted to the synthesis and study of new photosensitizers (a review is found in Brown, S. B. and Truscott, T. G., 1993). The development of more effective photochemotherapeutic agents requires the synthesis of compounds which absorb in the spectral region where living tissues are relatively transparent (i.e., 700–1000 nm), have high triplet quantum yields, and are minimally toxic. The present inventors'texaphyrin molecules absorb strongly in the tissue-transparent 730–770 nm range. The photophysical properties of metallotexaphyrins parallel those of the corresponding metalloporphyrins and the diamagnetic complexes sensitize the production of $^1O_2$ in high quantum yield The texaphyrins of the present invention, being completely synthetic, can be tuned so as to incorporate desired properties.

Photodynamic cleavage of DNA is known. Praseuth et al., reported cleavage of plasmid DNA by synthetic water-soluble porphyrins with visible light in the presence of oxygen. Fiel, R. J. (1989) also reported the photosensitized strand cleavage and oxidative-reductive strand scission of DNA by iron porphyrins. In another example, Kobayashi et al. reported cleavage of plasmid DNA by sodium pheophorbide (a derivative of chlorophyll) with visible light in the presence of oxygen. Porphyrinoligonucleotide derivatives were reportedly used to effect sequence specific modifications of DNA substrates followed by cleavage using hot piperidine (Vlassov et al., 1991; Le Doan et al., 1990). The absorption wavelengths for these porphyrin conjugates were below 700 nm, a range that does not penetrate tissue as effectively as longer wavelengths of light.

The use of ultraviolet light with the drug 8-methoxypsoralen to treat psoriasis is well established. Lee et al. relates to the interaction of psoralen-derivatized oligodeoxyribonucleoside methylphosphonates with single-stranded DNA. Crosslinked photoadducts between pyrimidines and psoralen appear to form. This treatment may result in the development of cancerous cells. Furthermore, irradiation at the short wavelength of about 365 nm does not penetrate the body and is therefore only useful on the body surface. Psoralen-based treatments must allow the drug to leave the body before the patient is exposed to visible light or the reaction will continue on the skin surface.

Sequence specific cleavage of DNA has also been reported for dark reactions using oligonucleotides derivatized with metal complexes. Some examples include oligonucleotide-EDTA-Fe complexes (Strobel, D. A. and P. B. Dervan, 1989; Lin, et al., 1989; Dreyer, G. B. and P. B. Dervan, 1985), oligonucleotide-tricationic porphyrins with metal binding appendages (Groves, J. T. and T. P. Farrell, 1989), oligonucleotide-phenanthroline-copper complexes (Chen, C. H. B. and D. S. Sigman, 1988), oligonucleotide-manganese-porphyrins (Meunier, B. et al., 1993), and iron-porphyrins linked to oligonucleotides (Le Doan et al., 1986, 1987).

Current photosensitive molecules lace good tumor selectivity, and require a short wavelength of light to effect the photoexcitation that is prerequisite to photosensitization.

The present invention relates to catalysts for the cleavage of RNA, in particular, photo-induced cleavage of RNA in a biological system. An effective photo-catalyst for PDT and RNA cleavage would have the following properties:

1. Easily available
2. Low intrinsic toxicity
3. Long wavelength absorption
4. Efficient photosensitizer for singlet oxygen production
5. Fair solubility in water
6. Selective uptake in lipophilic tissue such as atheroma or tumor tissue
7. Showing high affinity for enveloped viruses
8. Quick degradation and/or elimination after use
9. Chemically pure and stable
10. Easily subject to synthetic modification
11. Efficient at physiological temperature and pH
12. Specific for certain biological substrates
13. Easy administered to a biological system
14. Amenable to conjugation to site-directing carrier molecules.

The present inventors address these problems and provide herein photosensitizers having capability to cleave RNA, thereby providing a whole new range of targets for photodynamic therapy. These photosensitizers demonstrate tumor localization, absorption in the longer wavelength ranges up to about 800 nm, as well as non-toxicity, lack of skin photosensitivity, and ease of production in a pure form.

LIST OF ABBREVIATIONS

DCC: Dicyclohexylcarbodiimide
DMF: Dimethylformamide
EDTA: Ethylenediamine tetraacetic acid
NHS: N-hydroxysuccinimide
NM: Nanometers
TEA: Triethylamine
THF: Tetrahydrofuran
Txp (txph) (TX): Texaphyrin

SUMMARY OF THE INVENTION

The present invention provides a method of light-induced cleavage of a polymer of ribonucleic acid. The method comprises the steps of contacting the polymer with a photosensitive texaphyrin and exposing the photosensitive texaphyrin to light for a time sufficient to cleave the polymer. A texaphyrin as used herein is an aromatic pentadentate expanded porphyrin analog with appended functional groups. Such pendant groups may enhance solubility or biolocalization or may provide coupling sites for site-directing molecules such as oligonucleotides. The texaphyrin may be a metal complex of texaphyrin, preferred metals are diamagnetic metals.

The polymer may be a solution or a suspension of RNA or may be cellular RNA in vitro or in vivo. The ability to specifically photo-cleave RNA has important implications for the treatment of various diseases; for destruction of retroviral RNA, messenger RNA, ribosomal RNA, RNA cofactors, transfer RNA, small nuclear RNA, and small cytoplasmic RNA, thereby, providing a multifactorial approach to eliminating diseased, cancerous or other unwanted cells or tissues. A site of desired cleavage may be a position novel to undesired organisms in terms of health care. A site of desired cleavage may be a messenger RNA encoding a product deleterious to the host or may be a normal RNA that is deleterious in some way.

In the present light-dependent cleavage, the light may have a wavelength range of about 650–900 nm, preferably 700–800 nm, and most preferably 730–770 nm.

The cleavage of RNA described herein is a photolytic cleavage. It is believed that the cleavage is not hydrolytic where a water molecule is added across a bond to break the bond, nor is the cleavage believed to be solely oxidative where an oxidation reaction in the absence of light causes breakage of the bond.

The texaphyrin or texaphyrin metal complex for use in light-induced cleavage of a polymer of ribonucleic acid may have the structure:

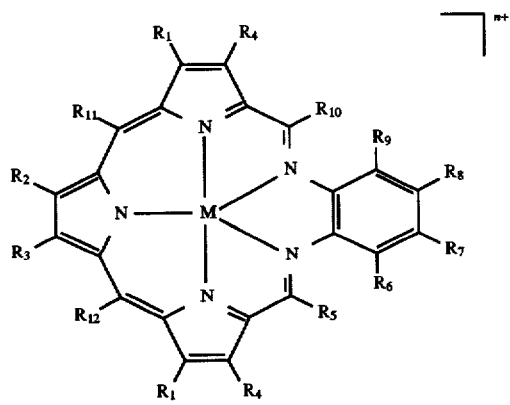

In this embodiment, M is H or a diamagnetic metal cation. $R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule; and n is an integer less than or equal to 5.

As used herein, a "site-directing molecule" may be an oligonucleotide, an antibody, a hormone, a peptide having affinity for a biological receptor, a sapphyrin molecule, and the like. A preferred site-directing molecule is an oligonucleotide, and the oligonucleotide may be an oligomer or polymer of a deoxyribonucleotide, a ribonucleotide, a modified oligoribonucleotide analog, a protein modified oligonucleotide, or an oligonucleotide linked via an amide, thiol, or oxy linkage. A preferred ribonucleotide analog, for example, has methyl groups on the 2' oxygen of the ribose. The O-methylation derivatization serves to protect the ribonucleotide from degradation. N, (n), will typically be an integer less than or equal to 5. In the context of the basic macrocycle with a divalent or trivalent metal cation, n is 1 or 2; however, one skilled in the art in light of the present disclosure would realize that the value of n would be altered due to charges present on substituents $R_1$–$R_{12}$ and charges present on the covalently bound site-directing molecule, for example, charges of the phosphate groups on an oligonucleotide.

The texaphyrin may be a texaphyrin metal complex, and in this embodiment, the metal M is a diamagnetic metal cation and the diamagnetic metal cation may be Lu(III), La(III), In(III), Y(III), Zn(II) or Cd(II).

The use of texaphyrin metal complexes to cleave RNA in vivo as a treatment procedure relies on the effective localization of the complex to the site of desired cleavage. A site of desired cleavage may be a position novel to undesired organisms in terms of health care. A site of desired cleavage may be an RNA encoding a product deleterious to the host or may be a normal RNA that is deleterious in some way.

The data of Example 5 demonstrate that diamagnetic metal-texaphyrin-oligonucleotide conjugates may be developed into RNA antisense reagents. This antisense strategy provides a clear and rational method for new drug design because there is one requirement, namely that the antisense probe hybridize to its target molecule. The hybridization requirement is very well understood via complementary Watson-Crick base-pairing. Unlike the present methods in the art which require screening of thousands of compounds and X-ray crystal structure analysis, the information needed for antisense technology is the sequence of the target. Treating native RNA with this new texaphyrin-oligonucleotide conjugate results in the conjugate binding to a complementary RNA sequence via the appended oligonucleotide. The diamagnetic metal-texaphyrin complex then cleaves the RNA proximal to this specific site. Two texaphyrin molecules may be attached to a conjugated oligonucleotide, enhancing the cleavage activity. Also, a greater number of texaphyrins attached to the oligonucleotide will cause the antisense agent to take on more of the pharmacodynamic and biodistribution properties of the texaphyrin, such as selective localization in tumors.

The texaphyrin oligonucleotide-conjugate would have immediate applications for anti-viral and anti-bacterial therapy as well as cancers (an oligonucleotide complementary to an oncogenic messenger RNA, for example) and inflammatory responses that are caused by the overexpression of certain proteins. Antisense technology is discussed in U.S. Pat. Nos. 5,194,428, 5,110,802 and 5,216,141, all of which are incorporated by reference herein. Metal-free and diamagnetic metallated texaphyrin compounds, methods for making and methods for using them are described in U.S. Pat. No. 4,935,498, 5,162,509, 5,252,720, 5,256,399; 5,272,142; 5,292,414; 5,369,101; 5,432,171; 5,439,570; 5,451,576; 5,457,183; and 5,475,104; and in allowed application U.S. Ser. No. 08/098,514, 08/196,964, 08/227,370, and 08/207,845; each patent and allowed application is incorporated by reference herein. Sapphyrin compounds are disclosed in U.S. Pat. Nos. 5,041,078, 5,159,065, 5,120,411, 5,302,714, and 5,457,195; each patent is incorporated by reference herein.

A method of treating a host harboring benign or malignant tumor cells is a further embodiment of the present invention. The method comprises administering to the host an effective amount of a photosensitive texaphyrin-oligonucleotide conjugate, the oligonucleotide having sequence complementarity to an RNA molecule of the benign or malignant tumor cells, and photoirradiating the photosensitive texaphyrin in proximity to the tumor cells. The photosensitive texaphyrin may be a texaphyrin complexed to a diamagnetic metal.

This method may further comprise the step of determining localization sites of the photosensitive texaphyrin in the host by reference to the texaphyrin. "By reference to the texaphyrin" as used herein means that the location may be found by localization such as magnetic resonance imaging if the texaphyrin contains a metal that is paramagnetic, gamma ray detection if the metal is gamma emitting, or by using monochromatic X-ray photon sources or fluorescent spectroscopy. Gamma emitting metals for radioimmunodiagnostics are described in U.S. Pat. No. 5,252,720, incorporated by reference herein. A preferred gamma emitting metal is $^{111}$In(III). The nonmetallated form of texaphyrin may be used, in particular, where fluorescence is the preferred means of detection of the texaphyrin. M may be H or $CH_3$ in a nonmetallated form of texaphyrin. A texaphyrin having a methyl group attached to a ring nitrogen (M is $CH_3$) is described in U.S. Pat. No. 5,457,183, incorporated by reference herein.

"Selective biolocalization" means having an inherently greater affinity for certain tissues relative to surrounding tissues. Texaphyrins have biolocalization specificity for lipid rich tissue, such as atheroma and tumor, for example. Importantly, hydroxylated texaphyrins have a lipid-water distribution coefficient that is optimal for localization to lipophilic regions, yet sufficiently water soluble to allow ease of handling.

Another embodiment of the present invention is a method for targeted intracellular RNA cleavage. The method comprises the introduction into a cell of a texaphyrin coupled to an oligonucleotide having complementary binding affinity for a targeted RNA, whereby cleavage of the targeted RNA is catalyzed by the texaphyrin. The RNA may be oncogenic messenger RNA, ribosomal RNA, transfer RNA, RNA cofactors, small nuclear RNA, or small cytoplasmic RNA which needs to be destroyed, for example, as part of tumor tissue or a pathogen. The oligonucleotide coupled to the texaphyrin may be DNA, a DNA analog, or an RNA analog oligonucleotide. The texaphyrin may be a free base texaphyrin or a metallated form of texaphyrin. The metal is preferably a diamagnetic metal, most preferably Lu(III).

A method for destroying messenger RNA, and thereby inhibiting the expression of a gene in an animal, comprising the administration to the animal of a texaphyrin oligonucleotide conjugate is a further embodiment of the present invention. The oligonucleotide has complementary binding affinity for regions of the messenger molecule or for small nuclear RNAs that are involved in the splicing reaction of messenger RNA. A further embodiment of the present invention is a method for inhibiting a tissue specific messenger RNA of an animal comprising administering to the animal a texaphyrin having specificity for the tissue. The texaphyrin may have appended an oligonucleotide complementary to the target messenger RNA.

A further embodiment of the present invention is a texaphyrin conjugate wherein two or more separate texaphyrin complexes are attached to an oligonucleotide, one at the 3', one at the 5'end, and/or one or more at an internal residue. The texaphyrin may be metal free or may be metallated. A metal ion of each of the texaphyrin complexes may be the same or it may be different. Similarly, each of the texaphyrins may be different. Use of a dual texaphyrin complex-conjugate should effect the cleavage of RNA with increased efficiency due to the concerted activity of the metal complexes. For diagnosis and treatment purposes, the administration of such a conjugate with one texaphyrin complex having a diamagnetic metal species and the other having a paramagnetic species would allow binding, imaging, and cleavage, all effected by one conjugate. In this case, binding is effected by the oligonucleotide, imaging is accomplished by MRI due to the presence of the paramagnetic metal ion, and cleavage is accomplished by the photosensitive texaphyrin containing a diamagnetic metal cation. Therefore, the biodistribution and cellular penetration of the conjugate may be determined.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1A:
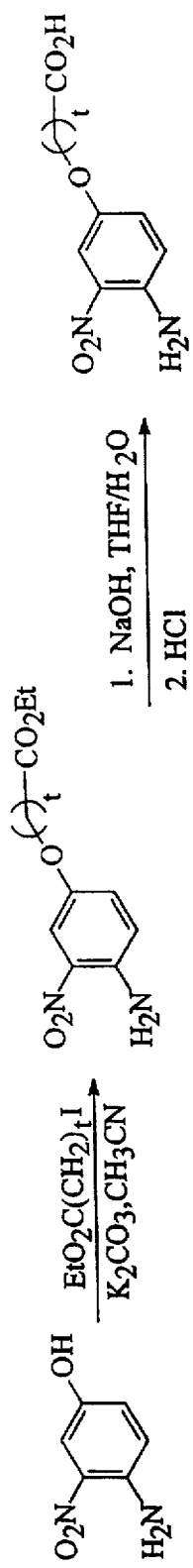
FIG. 1A.
Figure 1A:
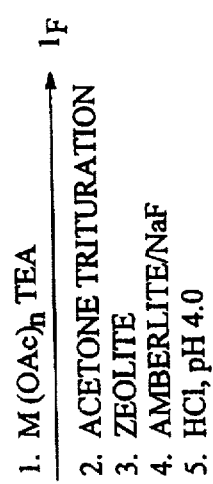
Figure 1A:
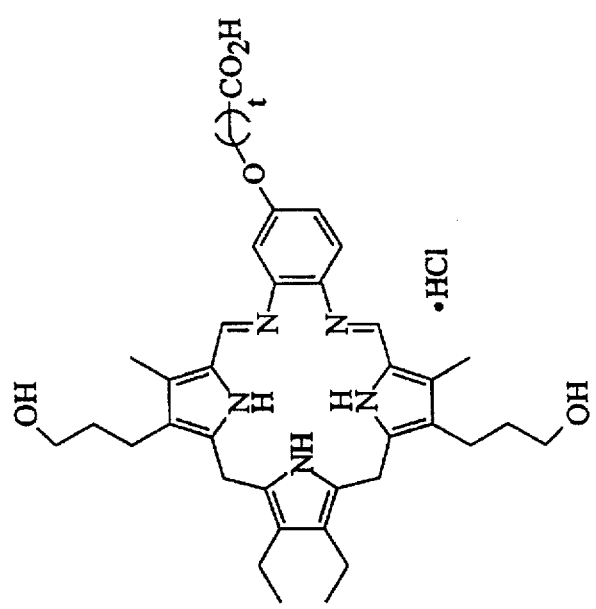
Figure 1A:
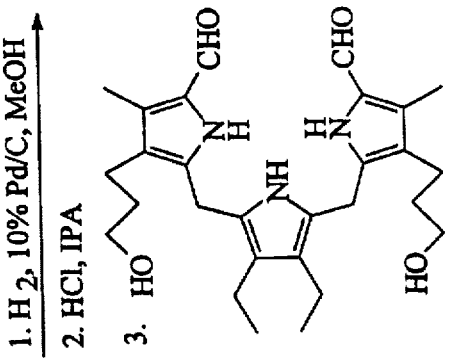

The present invention involves the use of photosensitive texaphyrins for the photodynamic treatment of tumor cells and other undesired cells and tissues in vivo and for the photoinduced cleavage of a polymer of ribonucleic acid. The photosensitive texaphyrin may be a free base texaphyrin or may be metallated with a diamagnetic metal. The term "photosensitive" means that upon irradiation, texaphyrin effects either the generation of oxygen products that are cytotoxic or means that the texaphyrin is fluorescent, or both. Cytotoxic oxygen products may be singlet oxygen, hydroxyl radicals, superoxide, or hydroperoxyl radicals.

In a presently preferred embodiment, the invention involves the site-specific cleavage of a ribonucleic acid using a photosensitive texaphyrin metal complex-oligonucleotide conjugate where the oligonucleotide is a site-directing molecule having sequence complementarity to a portion of the RNA to be cleaved. A preferred diamagnetic metal is Lu(III), La(III), In(III), Y(III), Zn(II), or Cd(II) and a most preferred diamagnetic metal is Lu(III) or Y(III).

An individual skilled in the art of organic synthesis in light of the present disclosure is able to prepare a large variety of photosensitive texaphyrins, all of which are expected to cleave RNA, an important biological species. Potential particular applications for this process include the photodynamic destruction of retroviral, messenger, ribosomal, transfer, small nuclear, and small cytoplasmic RNA, as well as RNA cofactors; thereby achieving a targeted light-induced therapeutic effect in the vicinity of a photosensitive molecule.

Texaphyrins of the present invention may be metal free or may be in a complex with a metal. For generating singlet oxygen, the preferred metal is a diamagnetic metal. Divalent and trivalent metal complexes of texaphyrins are by convention shown with a formal charge of $n^+$, where $n=1$ or 2, respectively. It is understood by those skilled in the art that the complexes described in the present invention have one or more additional ligands providing charge neutralization and/ or coordinative saturation to the metal ion. Such ligands include chloride, nitrate, acetate, and hydroxide, among others.

Texaphyrin metal complexes possess inherent biolocalization specificity as described in the '720 patent, localizing in lipid rich regions such as, for example, liver, kidney, tumor and atheroma. In one embodiment of the present invention, the texaphyrin metal complexes are further coupled to site-directing molecules to form conjugates for targeted in vivo delivery. "Site-directing" means having specificity for targeted sites. "Specificity for targeted sites" means that upon contacting the texaphyrin metal complex-conjugate with the targeted site, for example, under physiological conditions of ionic strength, temperature, pH and the like, specific binding will occur. The interaction may occur due to specific electrostatic, hydrophobic, entropic or other interaction of certain residues of the conjugate with specific residues of the target to form a stable complex under conditions effective to promote the interaction. In a preferred embodiment of the present invention, the interaction between a texaphyrin-deoxyoligonucleotide conjugate and the complementary ribonucleotide is an example of anti-sense technology and will allow cleavage of a polymer of ribonucleic acid that is in the vicinity of the specific binding. The inherent biolocalization properties of texaphyrin further effect targeting of an antisense agent to lipophilic regions, especially tumors and atheroma, for example.

A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds as described in the examples for attachment of oligonucleotides. In most preferred embodiments, oligonucleotides and other site-directing molecules are covalently bonded to the texaphyrin via a carbon-nitrogen, carbon-sulfur, or a carbon-oxygen bond.

The following structure shows a correlation of the IUPAC nomenclature for the positions of the atoms around the periphery of the macrocycle with the positions of the R groups of the present invention.

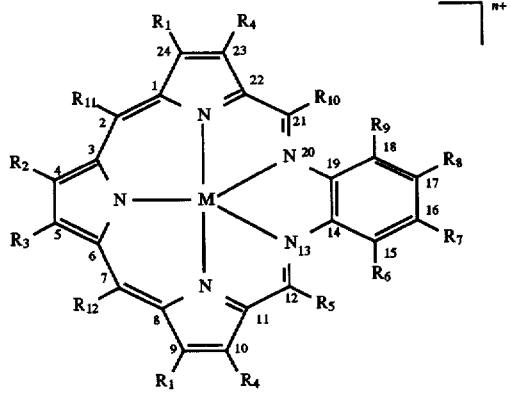

Substituents at the $R_6$ and $R_9$ positions on the B (benzene ring) portion of the macrocycle are incorporated into the macrocycle by their attachment to ortho-phenylenediamine in the 3 and 6 positions of the molecule. Substituents at the $R_5$ and $R_{10}$ positions on the T (tripyrrane) portion of the macrocycle are incorporated by appropriate functionalization of carboxyl groups in the 5 positions of the tripyrrane at a synthetic step prior to condensation with a substituted ortho-phenylenediamine.

The nonaromatic texaphyrin is conveniently produced by condensation of a tripyrrane aldehyde or ketone having structure A; and a substituted ortho-phenylenediamine having structure B:

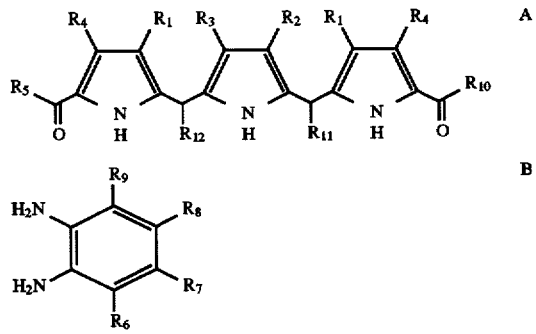

In this embodiment, $R_1-R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, a site-directing molecule, or a couple to a site-directing molecule. $R_6$ and $R_9$ are independently selected from the groups of $R_1-R_4$, $R_7$ and $R_8$, with the proviso that the halide is other than iodide and the haloalkyl is other than iodoalkyl. $R_5$, $R_{10}$, $R_{11}$ and $R_{12}$ are independently hydrogen, alkyl, aryl, hydroxyalkyl, oxyalkyl, oxyhydroxyalkyl, carboxyalkyl, carboxyamidealkyl or a couple to a saccharide, or to a site-directing molecule; and at least one of $R_5$, $R_6$, $R_9$, $R_{10}$, $R_{11}$ and $R_{12}$ is other than hydrogen.

In a preferred method of synthesis, the Brønsted base is triethylamine or N,N,N',N'-tetramethyl-1,8-diaminonaphthalene ("proton sponge") and the oxidant is air saturating the organic solvent, oxygen, platinum oxide, o-chloranil or 2,3-dichloro-5,6-dicyano-1,4-benzoquinone. The stirring or heating at reflux step may comprise stirring or heating at reflux the mixture for at least 24 hours and the organic solvent may comprise methanol, or methanol and chloroform, or methanol and benzene, or methanol and dimethylformamide.

In the texaphyrins of the present invention, the alkyl, aryl, hydroxyalkyl, oxyalkyl, oxyhydroxyalkyl, saccharide, carboxyalkyl, carboxyamidealkyl, site-directing molecule, or molecule couple is covalently bonded to the texaphyrin via a carbon-carbon, a carbon-nitrogen or a carbon-oxygen bond. The aryl may be a phenyl group, unsubstituted or substituted with a nitro, carboxy, sulfonic acid, hydroxy, oxyalkyl or halide substituent. In this case, the substituent on the phenyl group may be added in a synthetic step after the condensation step which forms the macrocycle.

Generally, water soluble texaphyrins retaining lipophilicity are preferred for the applications described herein. "Water soluble" means soluble in aqueous fluids to about 1 mM or better. "Retaining lipophilicity" means having greater affinity for lipid rich tissues or materials than surrounding nonlipid rich tissues or materials and, in the case of viruses in suspension, the term means having affinity for the membranous coat of the virus. "Lipid rich" means having a greater amount of triglyceride, cholesterol, fatty acids or the like.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by two or more functional groups as described herein.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

Representative examples of hydroxyalkyls include alcohols of methane, ethane, straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. The number of repeating oxyalkyls within a substituent may be up to 100, preferably is from 1–10, and more preferably, is 2–3. A preferred oxyalkyl is $O(CH_2CH_2O)_xCH_3$ where x=1–100, preferably 1–10, and more preferably, 2–3.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate substituted alkyls include alkyls as described above substituted by one or more sulfate groups, a representative example of which is diethyl sulfate $((C_2H_5)_2SO_4)$.

Representative examples of phosphates include phosphate or polyphosphate groups. Representative examples of phosphate substituted alkyls include alkyls as described above substituted by one or more phosphate or polyphosphate groups. Representative examples of phosphonate substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R'' is a functional group as described herein.

Representative examples of useful amines include a primary, secondary or tertiary amine of an alkyl as described hereinabove.

Exemplary site-directing molecules contemplated in the present invention include but are not limited to: polydeoxyribonucleotides, oligodeoxyribonucleotides, polyamides including peptides having affinity for a biological receptor and proteins such as antibodies; steroids and steroid derivatives; hormones such as estradiol, or histamine; hormone mimics such as morphine; and further macrocycles such as sapphyrins and rubyrins. The oligonucleotides may be derivatized at the bases, the sugars, the ends of the chains, or at the phosphate groups of the backbone to promote in vivo stability. Modifications of the phosphate groups are preferred in one embodiment of the invention since phosphate linkages are sensitive to nuclease activity. Preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include alkyl groups attached to an oxygen of a ribose moiety in a ribonucleotide. In particular, the alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides, and analogs thereof, are contemplated as site-directing molecules in the present invention.

The term "texaphyrin-oligonucleotide conjugate" means that an oligonucleotide is attached to the texaphyrin in a 5'or 3'linkage or both types of linkages to allow the texaphyrin to be an internal residue in the conjugate. The oligonucleotide or other site-directing molecule may be attached either directly to the texaphyrin via a linker, or a couple of variable length. During catalysis, for example, the texaphyrin portion of a texaphyrin metal complex-oligonucleotide conjugate is placed in the vicinity of the RNA substrate upon binding of the oligonucleotide to the targeted nucleic acid substrate. A "sapphyrin-oligonucleotide conjugate" is referred to in the same way as described above for a texaphyrin-oligonucleotide conjugate except that the texaphyrin is replaced with a sapphyrin.

Representative examples of useful oligonucleotides include nucleotides, oligonucleotides and polynucleotides primarily composed of adenine, cytosine, guanine, thymine or uracil bases. It is understood that the term nucleotide as used herein refers to both naturally-occurring and synthetic nucleotides, poly- and oligonucleotides and to analogs and derivatives thereof such as methylphosphonates, phosphotriesters, phosphorothioates and phosphoramidates.

Representative examples of useful steroids include any of the steroid hormones of the following five categories: progestins (e.g. progesterone), glucocorticoids (e.g., cortisol), mineralocorticoids (e.g., aldosterone), androgens (e.g., testosterone) and estrogens (e.g., estradiol).

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any of both naturally occurring and synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide; hexoses such as D-glucose, D-mannose or D-galactose; pentoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

For the above-described texaphyrins, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where in is a positive integer from 1 to 10, x is zero or a positive integer less than or equal to n, and y is zero or a positive integer less than or equal to ((2n+1)−2x).

The oxyhydroxyalkyl or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than ((2n+1)−q), q is zero or a positive integer less than or equal to 2n+1, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)−2w), R is H, alkyl, hydroxyalkyl, or $C_mH_{((2m+1)-r)}O_zR^b_r$, where m is a positive integer from 1 to 10, z is zero or a positive integer less than ((2m+1)−r), r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)−2w), R is H, alkyl, hydroxyalkyl, or $C_mH_{((2m+1)-r)}O_zR^b_r$, where m is a positive integer from 1 to 10, z is zero or a positive integer less than ((2m+1)−r), r is zero or a positive integer less than or equal to 2m+1, and $R^b$ is independently H, alkyl, hydroxyalkyl, or saccharide.

The carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than ((2n+1)−q), q is zero or a positive interger less than or equal to 2n+1, $R^c$ is $(CH_2)_nCO_2R^d$, $(CH_2)_nCONHR^d$ or $(CH_2)_nCON(R^d)_2$ where n is a positive integer from 1 to 10; $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to ((2m+1)−2w), R is H, alkyl, hydroxyalkyl, or $C_mH_{((2m+1)-r)}O_zR^b_r$, where m is a positive integer from 1 to 10, z is zero or a positive integer less than ((2m+1)−r), r is zero or a positive integer less than or equal to 2m+1, and $R^b$ is independently H, alkyl, hydroxyalkyl, or saccharide.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

For the above-described texaphyrins, the couple may be an amide, thiol, thioether or ether covalent bond, the oligonucleotide, the antibody, the hormone or the sapphyrin may have binding specificity for localization to a treatment site and the biological receptor may be localized to a treatment site.

Preferred functionalizations are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Other preferred functionalizations are where $R_6$ and $R_9$ are hydrogen, then $R_5$, $R_{10}$, $R_{11}$ and $R_{12}$ are lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl.

In a preferred embodiment of the present invention, at least one of $R_1$, $R_2$, $R_3$, $R_7$ and $R_8$ is a site-directing molecule or a couple that is coupled to a site-directing molecule. In a more preferred embodiment, at least one of $R_1$, $R_2$, $R_3$, $R_7$ and $R_8$ is an oligonucleotide, or a couple that is coupled to an oligonucleotide.

In a presently preferred texaphyrin, $R_1$ is $(CH_2)_2CH_2OH$, $R_2$ and $R_3$ are $CH_2CH_3$, $R_4$ is $CH_3$, $R_8$ is a site-directing molecule or a couple that is coupled to a site-directing molecule, and $R_7$ is H.

In another preferred texaphyrin, the substituent $R_1$ is $(CH_2)_2CH_2OH$, $R_2$ and $R_3$ are $CH_2CH_3$, $R_4$ is $CH_3$, $R_7$ is $O(CH_2CH_2O)_2CH_2CH_2OCH_3$, and $R_8$ is a site-directing molecule or a couple that is coupled to a site-directing molecule.

A couple that is coupled to an oligonucleotide may be further described as $O(CH_2)_tCO$-oligonucleotide where t is 1–7 and preferably 1–3.

In a further presently preferred embodiment, $R_1$ is $(CH_2)_2CH_2OH$, $R_2$ and $R_3$ are $CH_2CH_3$, $R_4$ is $CH_3$, and $R_7$ and $R_8$ are $O(CH_2CH_2O)_2CH_2CH_2OCH_3$. In other presently preferred embodiments, $R_1$–$R_4$, $R_7$, and $R_8$ are as in Table 1 for texaphyrins A1–A22.

In a further preferred embodiment of the above described method, the oligonucleotide has complementary binding affinity for an RNA in a region proximal to a cleavage site. The oligonucleotide may have complementary binding affinity for viral RNA, and upon cleavage by the texaphyrin-oligonucleotide conjugate, the virus would be killed. The oligonucleotide may have complementary binding affinity for oncogenic messenger RNA or may have binding specificity for localization to a treatment site. A hormone may have binding specificity for a biological receptor and the receptor is localized to a treatment site. The hormone or hormone mimic may be estradiol, histamine or morphine, for example.

Texaphyrins localize to tumors, atheroma, or can be site-directing via an attached site-directing molecule; they have absorption in the physiologically important range of 700–900 nm; they provide stable chelation for an otherwise toxic metallic cation, specificity for targeted sites in a therapeutic application, and are sufficiently nontoxic for in vivo use.

The method of site-specific cleavage of RNA involves at least two sources of specificity. A complementary oligonucleotide is designed to base-pair with the targeted substrate, providing a first source of specificity, and a second source of specificity for in vitro or in vivo applications is the positioning of the laser light. Such positioning of laser light, either by manual or mechanical means, would be particularly advantageous when the oligonucleotide cleavage reaction in question is to be effected at a particular biological locus, such as, for instance, a deep-seated tumor site. Here, the fact that the texaphyrins absorb light at wavelengths where bodily tissues are relatively transparent (700–900 nm) is particularly advantageous. This procedure allows for the effective implementation of light-based oligonucleotide strategies at loci deep within the body with relatively little deleterious light-based photosensitization of other tissues where the texaphyrin conjugates are not localized.

Hydroxylated texaphyrins described in U.S. Patent 5,252,720 and application 08/135,118 exhibit significant solubility in aqueous media, up to 1 mM or better, yet they retain affinity for lipid rich regions which allows them to be useful in a biological environment. Allowed U.S. Ser. No. 08/227,370 is incorporated by reference herein for the synthesis of texaphyrin oligonucleotide conjugates, particularly texaphyrin molecules where substituent $R_2$, $R_3$, $R_7$, or $R_8$ is an oligonucleotide or is a couple that is coupled to an oligonucleotide.

For the above-described uses, texaphyrins are provided as pharmaceutical preparations. A pharmaceutical preparation of a texaphyrin may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a texaphyrin of the present invention and the pharmaceutically acceptable carriers are then easily administered in a variety of dosage forms such as injectable solutions.

For parenteral administration, solutions of the texaphyrin in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary texaphyrins of the present invention are listed in Table 1.

TABLE 1

Representative Substituents for Texaphyrin Macrocycles of the Present Invention

| TXP | $R_1$ | $R_2$ | $R_3$ | $R_4$ | $R_8$ | $R_7$ |
|---|---|---|---|---|---|---|
| A1 | $CH_2(CH_2)_2OH$ | $CH_2CH_3$ | $CH_2CH_3$ | $CH_3$ | $O(CH_2)_3OH$ | $O(CH_2)_3OH$ |
| A2 | " | " | " | " | $O(CH_2CH_2O)_3CH_3$ | $O(CH_2CH_2O)_3CH_3$ |
| A3 | " | " | " | " | $O(CH_2)_tCON$-linker-site-directing molecule, t = 1–7 | " |
| A4 | " | " | " | " | $O(CH_2)_tCON$-linker-site-directing molecule | H |
| A5 | " | " | " | " | $OCH_2CO$-hormone | " |
| A6 | " | " | " | " | $O(CH_2CH_2O)_3CH_3$ | " |
| A7 | " | " | " | " | $OCH_2CON$-linker-site-directing molecule | $O(CH_2CH_2O)_3CH_3$ |
| A8 | " | " | " | " | $OCH_2CO$-hormone | " |
| A9 | " | " | " | " | $O(CH_2CH_2O)_{120}CH_3$ | $O(CH_2CH_2O)_3CH_2-CH_2-N$-imidazole |
| A10 | " | " | " | " | saccharide | H |
| A11 | " | " | " | " | $OCH_2CON(CH_2CH_2OH)_2$ | " |
| A12 | " | " | " | " | $CH_2CON(CH_3)CH_2-(CHOH)_4CH_2OH$ | " |
| A13 | " | COOH | COOH | " | $CH_2CON(CH_3)CH_2-(CHOH)_4CH_2OH$ | " |
| A14 | " | $COOCH_2CH_3$ | $COOCH_2CH_3$ | " | $CH_2CON(CH_3)CH_2-(CHOH)_4CH_2OH$ | " |
| A15 | $CH_2CH_2CON(CH_2CH_2OH)_2$ | $CH_2CH_3$ | $CH_2CH_3$ | " | $CH_2CON(CH_3)CH_2-(CHOH)_4CH_2OH$ | " |
| A16 | $CH_2CH_2ON(CH_3)CH_2-(CHOH)_4CH_2OH$ | " | " | " | $OCH_3$ | $OCH_3$ |
| A17 | $CH_2(CH_2)_2OH$ | " | " | " | $O(CH_2)_tCOOH$, t = 1–7 | H |
| A18 | " | " | " | " | $(CH_2)_t$-CON-linker-site-directing molecule, t = 1–7 | " |
| A19 | " | " | " | " | $YCOCH_2$-linker-site-directing molecule Y = NH, O | " |
| A20 | $CH_2CH_3$ | $CH_3$ | $CH_2CH_2COOH$ | " | $O(CH_2)_2CH_2OH$ | $O(CH_2)_2CH_2OH$ |
| A21 | " | " | $CH_2CH_2CO$ N-oligo | " | " | " |
| A22 | $CH_2(CH_2)_2OH$ | $CH_2CH_3$ | $CH_2CH_3$ | " | $O(CH_2)_3CO$-histamine | H |

Treatment of RNA with 1 μM LuB2T2 results in hydrolysis products in the absence, as well as the presence of light, (see Allowed U.S. Ser. No. 08/227,370, incorporated by reference herein). This reaction with RNA, therefore, is not photoinduced and produces different products than the photocleavage reaction of the present invention. photoxidatively damaged products include those involving reaction at position 9 of guanine, which generally leads to depurination, strand breakage, and the generation of two smaller pieces that both contain phosphorylated ends. Hydrolysis, on the other hand, leaves a free ribose on one of the two resulting fragments and a phosphate terminus on the other.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of a Lutetium Texaphyrin-Oligonucleotide Conjugate

Figure 1B:
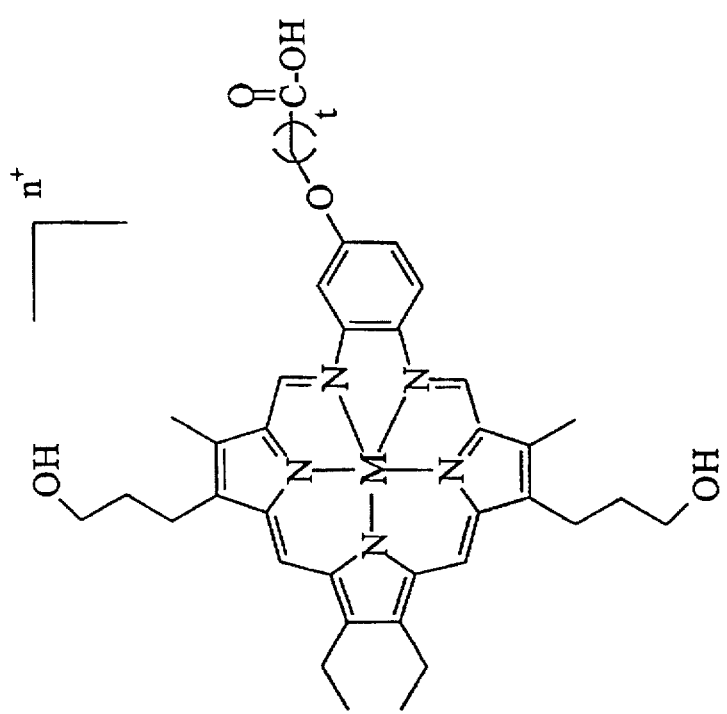
FIG. 1B, and FIG. 1C schematically summarize the synthesis of an oligonucleotide conjugate of a texaphyrin metal complex.
Figure 1C:
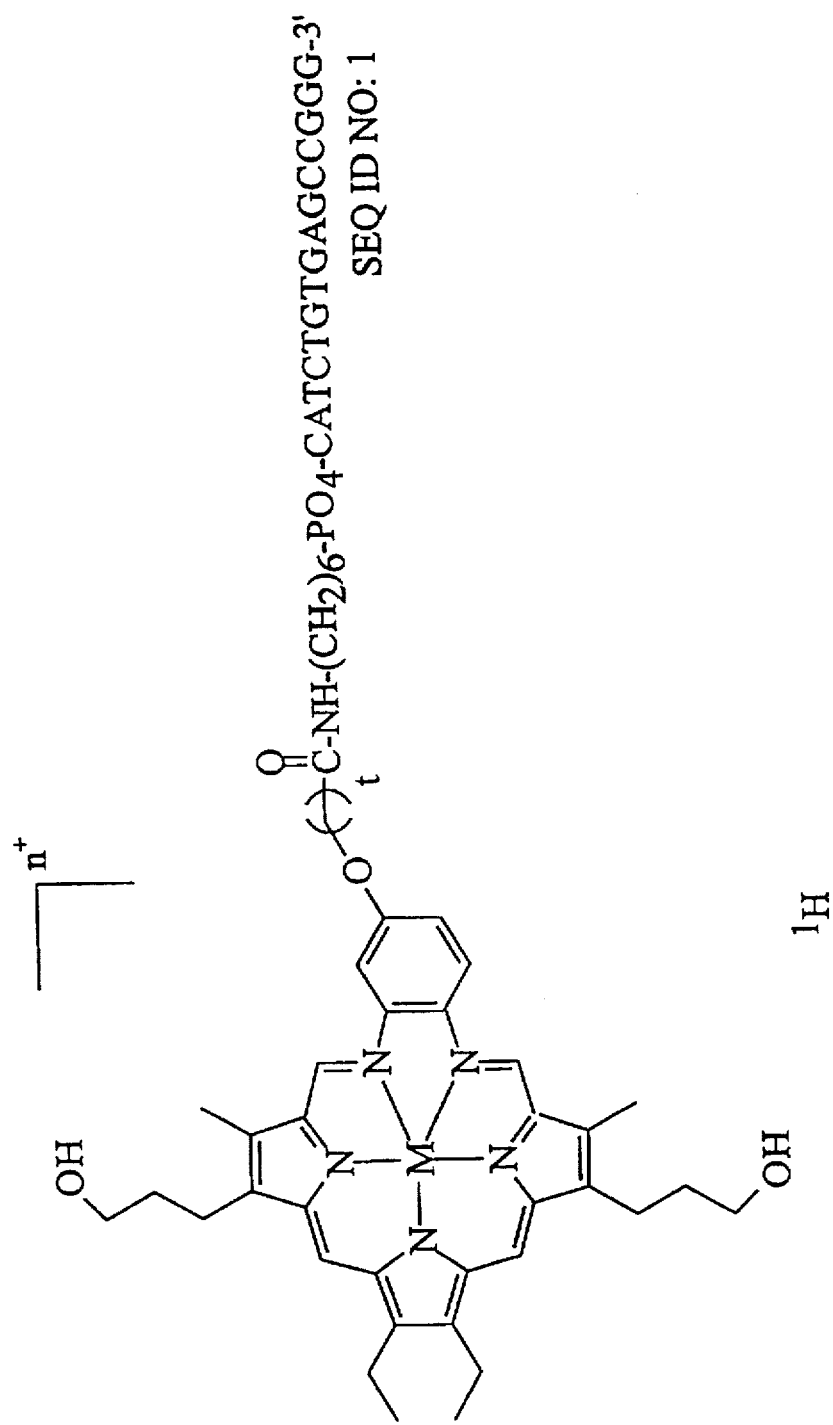

The present example provides for the synthesis of a lutetium texaphyrin-oligonucleotide conjugate useful for site-directed cleavage of a complementary RNA (see FIG. 1A, FIG. 1B, and FIG. 1C).

4-Amino-1-[1-(ethyloxy)acetyl-2-oxy]-3-nitrobenzene $1_B$, n=1. Potassium carbonate (14.0 g, 101 mmol and 4-amino-3-nitrophenol $1_A$ (10.0 g, 64.9 mmol) were suspended in 150 mL dry acetonitrile. Ethyl-2-iodoacetate (10 mL, 84.5 mmol) (or ethyl iodobutyrate may be used, in that case n=3) was added via syringe, and the suspension was stirred at ambient temperature for ca. 21 h. Chloroform (ca. 375 mL) was added and was used to transfer the suspension to a separatory funnel, whereupon it was washed with water (2×ca. 100 mL). The water washes were in turn washed with $CHCl_3$ (ca. 100 mL) and the combined $CHCl_3$ extracts were washed with water (ca. 100 mL). Solvents were removed on a rotary evaporator, and the residue was redissolved in $CHCl_3$ (ca. 500 mL) and precipitated into hexanes (1.5 L). After standing two days, the precipitate was filtered using a coarse fritted funnel and dried in vacuo to provide 14.67 g compound $1_B$, n=1 (94.1%). TLC: Rf=0.43, $CHCl_3$.

4-Amino-1-[1-(hydroxy)acetyl-2-oxy]-3-nitrobenzene $1_C$, n=1. 4-Amino-1-[1-(ethyloxy)acetyl-2-oxy]-3-nitrobenzene $1_B$, n=1, (10.00 g, 37.3 mmol) was dissolved in tetrahydrofuran (100 mL), aqueous sodium hydroxide (1M solution, 50 mL) was added and the solution was stirred at ambient temperature for ca. 21 h. Tetrahydrofuran was removed on a rotary evaporator, and water (100 mL) was added. The solution was washed with $CHCl_3$ (ca. 200 mL), then neutralized by addition of hydrochloric acid (1M solution, 50 mL). The precipitate which formed was filtered after standing a few minutes, washed with water, and dried in vacuo to provide 8.913 g compound $1_C$, n=1(99.5%). TLC: Rf=0.65, 10% methanol/$CHCl_3$.

16-[1-(Hydroxy)acetyl-2-oxy]-9,24-bis(3-hydroxypropyl)-4,5-diethyl-10,23-dimethyl-13,20,25,26, 27-pentaazapentacyclo[20.2.1.1$^{3,6}$.1$^{8,11}$.0$^{14,19}$]heptacosa-3, 5,8,10,12,14(19), 15,17,20,22,24-undecaene $1_E$, n=1.4-Amino-1-[1-(hydroxy)acetyl-2-oxy]-3-nitrobenzene $1_C$, n=1(1.800 g, 8.49 mmol) was dissolved in methanol (100 mL) in a 1 L flask. Palladium on carbon (10%, 180 mg) was added, and the atmosphere inside the flask was replaced with hydrogen at ambient pressure. A grey precipitate was formed after ca. 3 h, and the supernatant was clear. Methanol was removed in vacuo, taking precautions to prevent exposure to oxygen, and the compound was dried overnight in vacuo. Isopropyl alcohol (500 mL) and HCl (12M, 400 µL) were added, and the suspension was allowed to stir for ca. Bis[(3-hydroxypropyl-5-formyl-4-methylpyrrol-2-yl) methyl]-3,4-diethylpyrrole $1_D$ (n=1) (4.084 g, 8.49 mmol) was added, and the reaction stirred at room temperature under argon for 3 hours. Hydrochloric acid was again added (12M, 400 µL) and the reaction again was allowed to stir for an additional 3.5 h. The resulting red solution was filtered through celite, and the filtercake was washed with isopropyl alcohol until the filtrate was colorless. Solvent was reduced to a volume of ca. 50 mL using a rotary evaporator, whereupon the solution was precipitated into rapidly stirring $Et_2O$ (ca. 700 mL). Compound $1_E$ (n=1) was obtained as a red solid (5.550 g, 98.4%) upon filtering and drying in vacuo. TLC: R$_f$=0.69, 20% methanol/$CHCl_3$(streaks, turns green on plate with $I_2$).

Lutetium complex of 16-[1-(hydroxy)acetyl-2-oxy]-9,24-bis(3-hydroxypropyl)-4,5-diethyl-10,23-dimethyl-13,20,25, 26,27-pentaazapentacyclo[20.2.1.1$^{3,6}$.1$^{8,11}$.0$^{14,19}$] heptacosa-1,3,5,7,9,11(27),12,14(19),15,17,20,22(25),23-tridecaene $1_F$, M=Lu, n=1. Approximately equal molar amounts of the protonated form of the macrocycle, 16-[1-(hydroxy)acetyl-2-oxy]-9,24-bis(3-hydroxypropyl)-4,5-diethyl-10,23-dimethyl-13,20,25,26,27-pentaazapentacyclo [20.2.1.1$^{3,6}$.1$^{8,11}$.0$^{14,19}$]heptacosa-3,5,8,10,12,14(19),15,17, 20,22,24-undecaene hydrochloride $1_E$, n=1, and a lutetium acetate pentahydrate were combined with triethylamine in methanol, and heated to reflux under air for 5.5 h. The reaction was cooled to room temperature, and stored at −20° C. overnight. Solvent was removed on a rotary evaporator, acetone was added, and the suspension was stirred on a rotary evaporator for 2 h. The suspension was filtered and the precipitate dried briefly in vacuo, whereupon a solution was formed in methanol (ca. 250 mL) and water (25 mL). The pH was adjusted to 4.0 using HCl (1M). HCl-washed zeolite LZY54 was added (ca. 5 g) and the suspension was stirred on the rotary evaporator for ca. 6 h. Amberlite™ IRA-900 ion exchange resin (NaF treated, ca. 5 g) was added, and the suspension was stirred for an additional hour. The suspension was filtered, the resin was washed with methanol (ca. 100 mL), and the filtrate was adjusted to pH 4.0 using HCl (1M). Solvents were removed on a rotary evaporator, using ethanol (abs.) to remove traces of water. After drying in vacuo, the compound was dissolved in methanol (25 mL) and precipitated into rapidly stirring $Et_2O$ (300 mL). Compound $1_F$, M=Lu and n=1, was obtained as a precipitate after filtering and drying in vacuo. An analytical sample was prepared by treating 50 mg of $1_F$, n=1, dissolved in methanol (25 mL) with acetic acid-washed zeolite, then acetic acid-washed Amberlite™ for ca. 1 h. After reducing methanol to a minimum volume, the solution was precipitated into rapidly stirring $Et_2O$ (70 mL), filtered, and dried in vacuo.

Postsynthetic modification of oligodeoxynucleotide-amine $1_G$ with lutetium texaphyrin complex $1_F$, n=1. The lutetium complex of 16-[1-(hydroxy)acetyl-2-oxy]-9,24-bis (3-hydroxypropyl)-4,5-diethyl-10,23-dimethyl-13,20,25,26, 27-pentaazapentacyclo[20.2.1.1$^{3,6}$.1$^{8,11}$.0$^{14,19}$]heptacosa-1, 3,5,7,9,11(27),12,14(19),15,17,20,22(25),23-tridecaene $1_F$, M=Lu, n=1, (about 30 µmol) and N-hydroxysuccinimide (43 µmol) were dried together overnight in vacuo. The compounds were dissolved in dimethylformamide (anhydrous, 500 µL) and dicyclohexylcarbodiimide (10 mg, 48 µmol) was added. The resulting solution was stirred under argon with protection from light for 8h, whereupon a 110 µL aliquot was added to a solution oligodeoxynucleotide $1_G$ (87 nmol) in a volume of 350 µL of 0.4 M sodium bicarbonate buffer in a 1.6 mL Eppendorf tube. After vortexing briefly, the solution was allowed to stand for 23 h with light protection. The suspension was filtered through 0.45 µm nylon microfilterfuge tubes, and the Eppendorf tube was washed with 150 µL sterile water. The combined filtrates were divided into two Eppendorf tubes, and glycogen (20 mg/mL, 2 µL) and sodium acetate (3M, pH 5.4, 30 µL) were added to each tube. After vortexing, ethanol (absolute, 1 mL) was added to each tube to precipitate the DNA. Ethanol was decanted following centrifugation, and the DNA was washed with an additional 1 mL aliquot of ethanol and allowed to air dry. The pellet was dissolved in 50% formamide gel loading buffer (20 µL), denatured at 90° C. for ca. 2′, and loaded on a 20% denaturing polyacrylamide gel. The band corresponding to conjugate $1_H$ M=Lu, n=1, was cut from the gel, crushed, and soaked in 1× TBE buffer (ca. 7 mL) for 1–2 days. The suspension was filtered through nylon filters (0.45 µm) and desalted using a Sep-pak™ reverse phase cartridge. The conjugate was eluted from the cartridge using 40% acetonitrile, lyophilized overnight, and dissolved in 1 mM HEPES buffer, pH 7.0 (500 µL). The solution concentration was determined using UV/vis spectroscopy.

EXAMPLE 2

Synthesis of texaphyrins or texaphyrin metal complexes with amine-, thiol- or hydroxy-linked oligonucleotides Amides, ethers, and thioethers are representative of linkages which may be used for coupling site-directing molecules such as oligonucleotides to texaphyrins or texaphyrin metal complexes. Allowed U.S. Ser. No. 08/227,370 is incorporated by reference herein for providing syntheses of texaphyrin-oligonucleotide conjugates having these types of linkages or couples.

Site-directing molecules having an amine functionality or oligonucleotides functionalized with an amine at the 5'-end, the 3'-end, or internally at sugar or base residues are modified post-synthetically with an activated carboxylic ester derivative of a texaphyrin or texaphyrin metal complex. In the presence of a Lewis acid such as FeBr$_3$, a bromide derivatized texaphyrin will react with an hydroxyl group of an oligonucleotide to form an ether linkage between the texaphyrin linker and the oligonucleotide.

Alternatively, oligonucleotide analogues containing one or more thiophosphate or thiol groups are selectively alkylated at the sulfur atom(s) with an alkyl halide derivative of the texaphyrin complex. Oligodeoxynucleotide-complex conjugates are designed so as to provide optimal catalytic interaction between the targeted RNA phosphodiester backbone and the texaphyrin.

In the present invention, oligonucleotides are used to bind selectively compounds that include the complementary ribonucleotide, or oligoribonucleotide, or polyribonucleotide containing a substantially complementary sequence. As used herein, a substantially complementary sequence is one in which the nucleotides generally base pair with the complementary nucleotide and in which there are very few base pair mismatches. The oligonucleotide may be large enough to bind probably at least 9 nucleotides of complementary nucleic acid.

The present inventors envision the texaphyrin-oligonucleotide conjugates of the present invention as being chemotherapeutic agents, for example, in an antisense capacity.

For general reviews of synthesis of DNA, RNA, and their analogues, see Oligonucleotides and Analogues, F. Eckstein, Ed., 1991, IRL Press, New York; *Oligonucleotide Synthesis*, M. J. Gait, Ed., 1984, IRL Press Oxford, England; Caracciolo et al. (1989); *Bioconjugate Chemistry*, Goodchild, J. (1990); or for phosphonate synthesis, Matteucci, MD. et al., *Nucleic Acids Res.* 14:5399 (1986).

In general, there are three commonly used solid phase-based approaches to the synthesis of oligonucleotides containing conventional 5'-3' linkages. These are the phosphoramidite method, the phosphonate method, and the triester method.

A brief description of a current method used commercially to synthesize oligomeric DNA is as follows: Oligomers up to ca. 100 residues in length are prepared on a commercial synthesizer, e.g., Applied Biosystems Inc. (ABI) model 392, that uses phosphoramidite chemistry. DNA is synthesized from the 3' to the 5' direction through the sequential addition of highly reactive phosphorous(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add a further residue until the desired DNA polymer is synthesized. The full length polymer is released from the solid support, with concomitant removal of remaining protective groups, by exposure to base. A common protocol uses saturated ethanolic ammonia.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete. The phosphonates can also be converted to phosphoramidate derivatives by reaction with a primary or secondary amine in the presence of carbon tetrachloride.

In the triester synthesis, a protected phosphodiester nucleotide is condensed with the free hydroxyl of a growing nucleotide chain derivatized to a solid support in the presence of coupling agent. The reaction yields a protected phosphate linkage which may be treated with an oximate solution to form unprotected oligonucleotide.

To indicate the three approaches generically, the incoming nucleotide is regarded as having an "activated" phosphite/phosphate group. In addition to employing commonly used solid phase synthesis techniques, oligonucleotides may also be synthesized using solution phase methods such as diester synthesis. The methods are workable, but in general, less efficient for oligonucleotides of any substantial length.

Preferred oligonucleotides resistant to in vivo hydrolysis may contain a phosphorothioate substitution at each base (*J. Org. Chem.*, 55:4693–4699, (1990) and Agrawal, (1990)). Oligodeoxy-nucleotides or their phosphorothioate analogues may be synthesized using an Applied Biosystem 380B DNA synthesizer (Applied Biosystems, Inc., Foster City, Calif.).

EXAMPLE 3

Synthesis of a Texaphyrin-Oligonucleotide Conjugate Having a Texaphyrin Attached to the 3' End of the Oligonucleotide Two oligodeoxyribonucleotides of 12 bases each were synthesized to contain alkylamine groups at the 3' terminal phosphate (Keystone Labs, Menlo Park, Calif.). Oligonucleotides were HPLC purified and precipitated using LiCl prior to use. Reaction of a carboxylic acid functionalized metal texaphyrin complex, such as the Lu(III)texaphyrin complex, with carbodiimide and N-hydroxysuccinimide produced the corresponding activated ester, which was added directly to a solution of the chosen oligodeoxynucleotide amine. The resulting texaphyrinmetal complex-oligonucleotide conjugates were purified by electrophoresis.

These 3'-conjugates may be of particular importance in certain embodiments of the present invention, since attachment of large groups (such as the present texaphyrin complexes) to the 3' end of an oligonucleotide renders the oligonucleotide resistant to cellular exonucleases.

In a similar manner, an embodiment of the present invention is the addition of particular ligands to the 3' end of an oligonucleotide having its 5' end conjugated to a texaphyrin. The function of the 3' ligand is to aid in the uptake of the conjugate into the cell. Such ligands are known in the art and include, but are not limited to, cholesterol and polylysine.

A further embodiment of the present invention in the cleavage of RNA using a texaphyrin or texaphyrin-metal complex-oligonucleotide conjugate is the use of a set of two conjugates, one having the texaphyrin conjugated to the 5' end of an oligomer and the other having a texaphyrin conjugated to the 3' end of an oligomer and the oligomers are complementary to the same RNA substrate, one just upstream from the other, so as to position both texaphyrins in proximity to the targeted cleavage site. The distance separating the two catalytic groups may be varied by preparing a nested set of oligomer-5' -conjugates of varying lengths and comparing the cleavage efficiencies that result upon the simultaneous binding of the two conjugates to the RNA template.

EXAMPLE 4

Synthesis of a Texaphyrin-Oigonucleotide Dual Conjugate

An oligodeoxyribonucleotide having 12 bases was synthesized to contain alkylamine groups at both the 3' and the 5' ends (Keystone Labs, Menlo Park, Calif.). This oligomer was reacted with an excess of a carboxylic acid functionalized metal-texaphyrin complex, following the procedures of Example 3, to give a dual conjugate having a texaphyrin-metal complex at both the 3'-and the 5'-ends of the 12-mer.

The use of two texaphyrins conjugated to the same oligonucleotide, one at each end, should effect the cleavage of RNA with increased efficiency due to the concerted activity of the metal complexes. In this embodiment, if the texaphyrin is metallated, it is preferred that both of the texaphyrin complexes contain the same metal, preferably a diamagnetic metal cation and more preferably lutetium(III).

Further, a dual conjugate provides versatility in the functions that may be accomplished by this one molecule. For example, the oligonucleotide provides binding specificity, one texaphyrin metal complex may provide for imaging (having Gd(III) as the metal ion, for example) while the other provides for RNA cleavage. Such a dual conjugate allows for 2 functions, imaging and cleavage, to be effected by one molecule.

EXANMPLE 5

Site-Specific Light-Dependent Cleavage of RNA by LuTxp-Oligonucleotide Conjugate The present example provides for the site-specific light-dependent leavage of RNA by four different lutetium texaphyrin-oligonucleotide conjugates. Cleavage of the corresponding DNA substrates by the texaphyrin oligonucleotide conjugates serves as a control study and demonstrates that cleavage occurs at guanine residues with the RNA and DNA substrates.

Figure 2A:
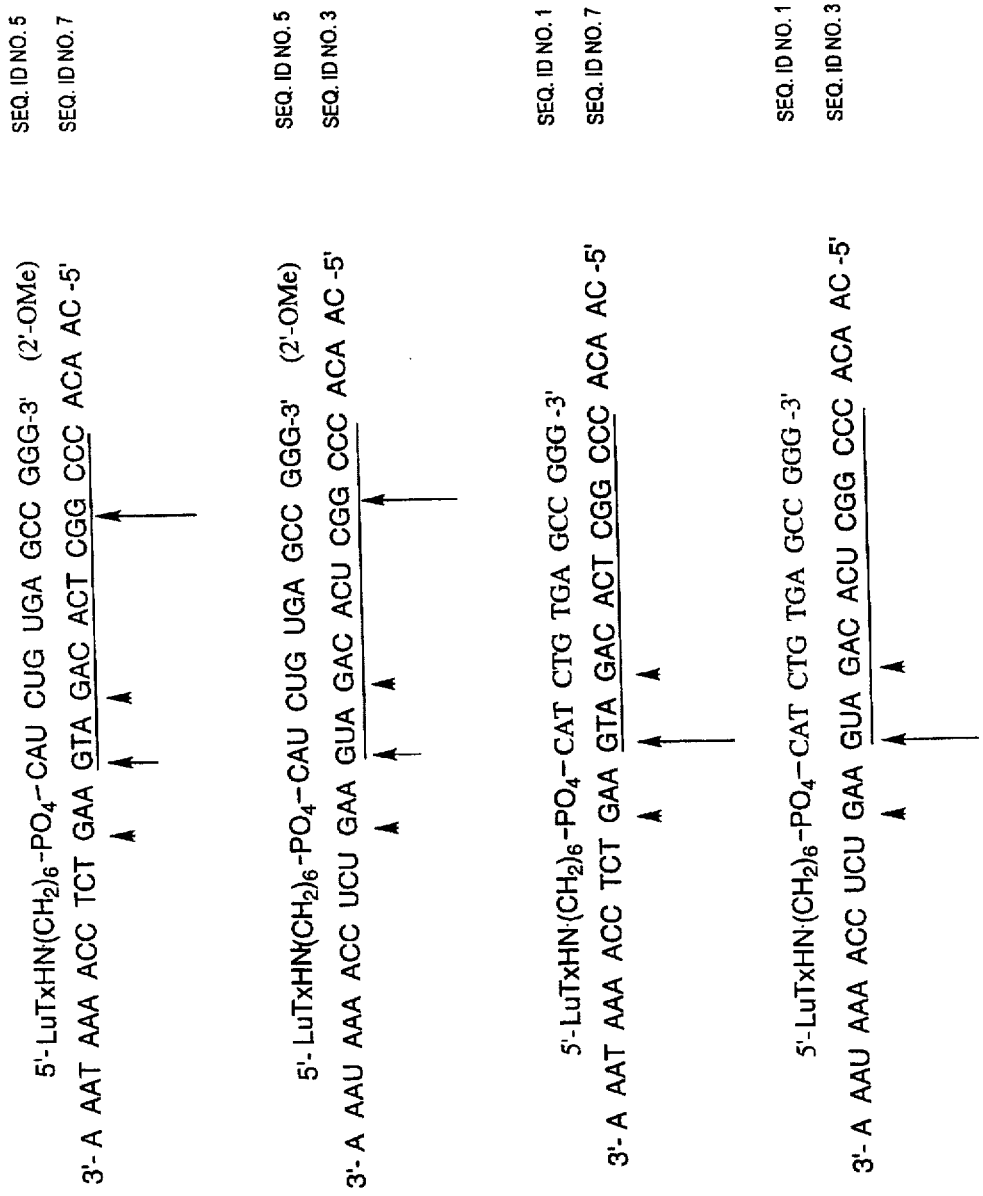
FIG. 2A and FIG. 2B demonstrate exemplary texaphyrin oligonucleotide conjugates of the present invention base-paired with DNA or RNA substrates. The arrows indicate observed sites of cleavage.
Figure 2B:
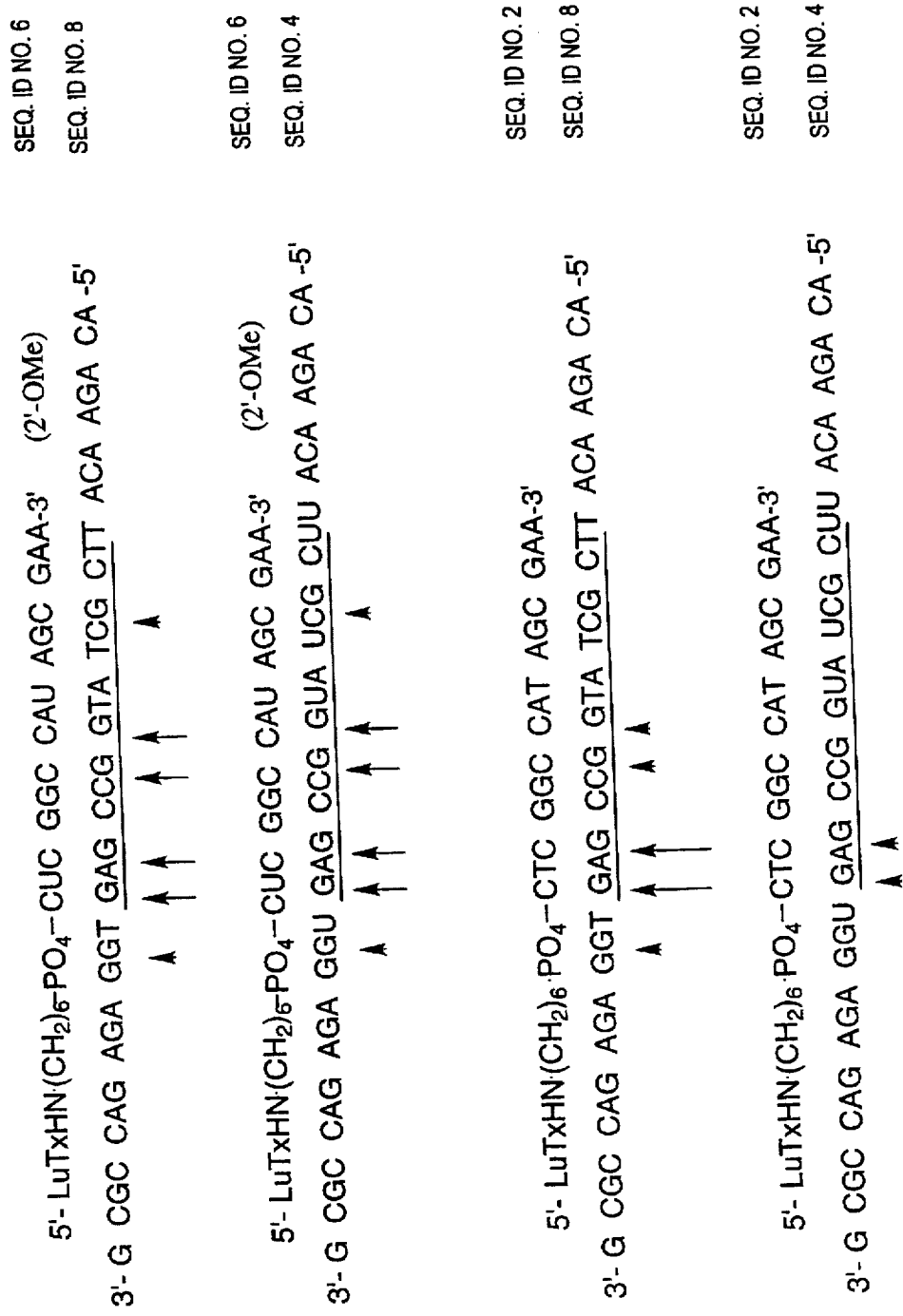

Reaction mixtures were prepared by adding ca. 100,000 cpm of 5'-$^{32}$P-labeled RNA 36-mer or DNA 36-mer substrate to solutions made from lutetium texaphyrin-oligonucleotide conjugate as shown in FIG. 2A and FIG. 2B, 4× buffer (5 µL), carrier DNA (1 µL) and water to produce a final volume of 20 µL. Final conjugate concentration was 50 nM. The 4– buffer is 400 mM NaCl, 200 mM HEPES, pH 7.5, 100 µM EDTA. All samples were irradiated for 15 minutes at ambient temperature using a dye laser (Coherent, Palo Alto, Calif.) tuned to 732 nm using a power density of 150 mW/cm$^2$. Following irradiation, the RNA or DNA was precipitated with ethanol using standard methods.

Samples containing radiolabeled DNA were dissolved in 10% aqueous piperidine solution (50 µL) and heated at 90° C. for 30 minutes. Samples containing radiolabeled RNA were dissolved in 1:1:8 aniline/acetic acid/water (50 µL) and heated at 58° C. for 30 minutes. Water (500 µL) was added to all samples, which were then dried on a Speedvac. All samples were resuspended in 50% formamide loading buffer, denatured at 60° C. for 5 minutes, and analyzed by electrophoresis on a 20% denaturing polyacrylamide gel.

The autoradiograph indicated substantial cleavage only in those lanes that contained the appropriate complementary 15-mer LuTx conjugate. A texaphyrin conjugated to a non-complementary oligonucleotide did not effect cleavage of the substrate. The Lu-Tx-mediated cleavage bands comigrated with bands generated by dimethylsulfate in guanine-specific sequencing lanes run as a control. The intensity of cleavage was greater at sites proximal to the expected location of the LuTx complex. These observations are consistent with a model whereby hybridization of the LuTx conjugates to their complementary sequences of RNA or DNA effects site-specific photomodification at guanine residues, and results in site-specific photocleavage upon workup under basic conditions.

In comparing 2'-O-methyl RNA and DNA oligonucleotide conjugates, a greater degree of cleavage was found to occur at lower positions on the gel, corresponding to photomodification at sites along and across the major groove of the duplex formed between antisense conjugate and target. These differences in cleavage pattern apparently relate to conformational differences between 2'-O-methyl RNA- and DNA-derived duplexes, with 2'-O-methyl RNA conjugates leading to a greater overall cleavage efficiency.

Cleavage efficiency ranged from 70–90% for the DNA substrates. Cleavage patterns of RNA substrates paralleled that of their DNA analogues, albeit occurring in lower yield. This likely reflects less efficient exposure of the photoinduced lesions by the milder aniline treatment. (The RNA was not subjected to the piperidine treatment due to its greater lability under alkaline conditions). The combination of substrate SEQ ID NO: 4 and texaphyrin-oligonucleotide conjugate labeled SEQ ID NO: 2 showed relatively little photocleavage in comparison to other lanes containing complementary conjugate. This may indicate poorer binding of the DNA-LuTx conjugate to this RNA sequence, and further evidences the superiority of the 2'-O-methyl RNA conjugate as used in this application.

Although the present inventors were aware of texaphyrins having photocleavage activity for polymers of DNA (U.S. Ser. No. 08/310,501), it was not clear that RNA would also be photocleaved. The 2' site is protected by a hydroxyl group in RNA, the conformation of the polymer is different than DNA, and the electronic effects from the C9 position of guanine are different than in DNA. Even though the cleavage demonstrated in this example is with a texaphyrin conjugated to an oligonucleotide, the inventors expect that unconjugated texaphyrin would be effective at cleavage also, although at higher concentrations than used herein.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods, and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

Brown, S. B. and T. G. Truscott., *Chemistry in Britain*, 955–958, Nov. 1993.

Caracciolo et al. *Science*, 245:1107, 1989.

Chen, C. H. B. and Sigman, D. S., *J. Amer. Chem. Soc.*, 110:6570–6572, 1988.

Dervan, *Science*, 232:464–471, 1986.

Dreyer and Drevan, *Proc. Natl. Acad. Sci. USA*, 82:968–972, 1985.

Fiel, *Journal of Biomolecular Structure & Dynamics*, 6(6):1259–1275, 1989.

Goodchild, J., *Bioconjugate Chemistry*, 1:165–187, 1990.

Grossweiner, L. I., *Lasers, Surg. Med.*, 11:165–173, (1991).

Groves and Farrell, J. *Am. Chem. Soc.*, 111:4998–5000, 1989.

Henderson, B. W. and T. J. Dougherty, *Photochem., Photobiol.*, 55:145–157, 1992.

Kobayashi, et al., *Photomed. Photobiol.*, 15 (1993).

Le Doan et al., *Biochemistry*, 25:6736–6739, 1986.

Le Doan et al., *Bioconjugate Chem.*, 1:108 (1990).

Le Doan et al., *Nucleic Acids Research*, 15(21):8643–8659, 1987.

Lee et al., *Biochemistry*, 27:3197–3203, 1988.

Lin, et al., *Biochemistry*, 28:1054–1061, 1989.

Meunier, B., et al., *Bioconjugate Chem.*, 4:366–371.

Moan, J. and K. Berg, *Photochem. Photobiol.*, 55:931–948, 1992.

PCT/US94/06284.

Praseuth et al., *Photochemistry and Photobiology*, 44:717–724, 1986.

Sessler et al., *Comm. Inorg. Chem.*, 7:333, 1988.

Sessler et al., *SPIE Proc. Soc. Opt. Eng.*, 1426:318–329, 1991.

Sindelar et al., *Arch. Surg.*, 126:318–324, 1991.

Skikes, J. D., *Photochem. Photobiol.*, 43:691, 1986.

Strobel and Dervan, J. *Am. Chem. Soc.*, 111(18):7826–7827, 1989.

U.S. Pat. No. 4,935,498.

U.S. Pat. No. 5,162,509.

U.S. Pat. No. 5,252,720.

U.S. Ser. No. 08/112,872.

U.S. Ser. No. 08/227,370.

Vlassov et al., *Nucleosides & Nucleotides*, 10(103:641–643, 1991.

What is claimed is:

1. A method of light-induced cleavage of a polymer of ribonucleic acid, the method comprising:

contacting the polymer with a photosensitive texaphyrin; and exposing the photosensitive texaphyrin to light for a time sufficient to cleave the polymer.

2. The method of claim 1 where the photosensitive texaphyrin has the structure:

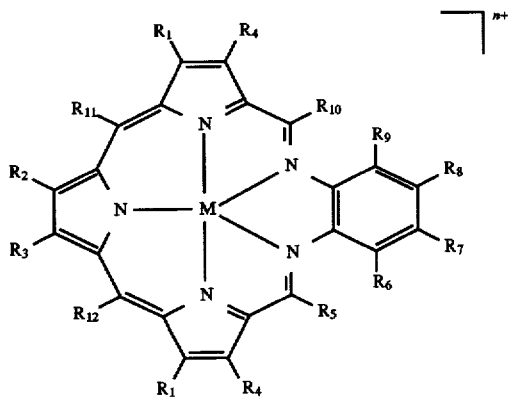

wherein

M is H or a diamagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide, or to a site-directing molecule; and n is an integer less than or equal to 5.

3. The method of claim 2 wherein the site-directing molecule is an oligonucleotide, an antibody, a hormone, a peptide having affinity for a biological receptor, or a sapphyrin molecule.

4. The method of claim 2 wherein at least one of $R_1$, $R_2$, $R_3$, $R_7$ and $R_8$ is a site-directing molecule, or a couple that is coupled to a site-directing molecule.

5. The method of claim 2 wherein at least one of $R_1$, $R_2$, $R_3$, $R_7$ and $R_8$ is an oligonucleotide, or a couple that is coupled to an oligonucleotide.

6. The method of claim 2 wherein $R_1$ is $(CH_2)_2CH_2OH$, $R_2$ and $R_3$ are $CH_2CH_3$, $R_4$ is $CH_3$, $R_8$ is a site-directing molecule, or a couple that is coupled to a site-directing molecule, and $R_7$ is H.

7. The method of claim 2 where $R_1$ is $(CH_2)_2CH_2OH$, $R_2$ and $R_3$ are $CH_2CH_3$, $R_4$ is $CH_3$, $R_7$ is $O(CH_2CH_2O)_2 CH_2CH_2OCH_3$, and $R_8$ is a site-directing molecule, or a couple that is coupled to a site-directing molecule.

8. The method of claim 2 wherein $R_1$ is $(CH_2)_2CH_2OH$, $R_2$ and $R_3$ are $CH_2CH_3$, $R_4$ is $CH_3$, and $R_7$ and $R_8$ are $O(CH_2CH_2O)_2CH_2CH_2OCH_3$.

9. The method of claim 2 wherein $R_1$–$R_4$, $R_7$, and $R_8$ are as in Table 1 for texaphyrins A1–A22.

10. The method of claim 2 wherein M is a diamagnetic metal cation and the diamagnetic metal cation is Lu(III), La(III), In(III), Y(III), Zn(II) or Cd(II).

11. The method of claim 2 wherein M is a diamagnetic metal cation and the diamagnetic metal cation is Lu(III).

12. The method of claim 1 wherein the light has a wavelength range of about 700 to 800 nanometers.

13. The method of claim 2 where $R_1$ is $(CH_2)_2CH_2OH$; $R_2$ and $R_3$ are $CH_2CH_3$; $R_4$ is $CH_3$; $R_7$ is $OCH_3$; and $R_8$ is a site-directing molecule, or a couple that is coupled to a site-directing molecule.

14. The method of claim 7 where the site-directing molecule is an oligonucleotide.

15. The method of claim 13 where the site-directing molecule is an oligonucleotide.

* * * * *

UNITED STATES PATENT AND TRADEMARK OFFICE
CERTIFICATE OF CORRECTION

PATENT NO.: 5,714,328

DATED: February 3, 1998

INVENTOR: Magda et al.

It is certified that errors appear in the above-identified patent and that said Letters Patent is hereby corrected as shown below:

On the title page:

In column 1, item [73], delete "the" and substitute --The--, therefor.

In Claim 13, column 28, line 41, insert a space between 'R$_7$' and 'is'.

Signed and Sealed this

Second Day of June, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO : 5,714,328
DATED : February 3, 1998
INVENTOR(S): Magda, et al.

It is certified that error appears in the above-identified patent and that said Letters Patent is hereby corrected as shown below:

At column 1, immediately following the title, please insert the following paragraph:

-- The government may own certain rights in the present invention pursuant to one or more of the following: National Institutes of Health Grants CA68682, AI28845 and AI33577; and National Science Foundation Grants CHE8552768 and CHE9122161.--

Signed and Sealed this

Sixth Day of June, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:1:

CATCTGTGAG CCGGG                               15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:2:

CTCGGCCATA GCGAA                               15

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA"

( x i ) SEQUENCE DESCRIPTION: SEQ ID NO:3:

CAACACCCGG CUCACAGAUG AAGUCUCCAA AAUAAA    36

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA"

( x i ) SEQUENCE DESCRIPTION: SEQ ID NO:4:

ACAGAACAUU CGCUAUGGCC GAGUGGAGAG ACCGCG    36

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA"

( x i ) SEQUENCE DESCRIPTION: SEQ ID NO:5:

CAUCUGUGAG CCGGG    15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "RNA"

( x i ) SEQUENCE DESCRIPTION: SEQ ID NO:6:

CUCGGCCAUA GCGAA    15

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:7:

CAACACCCGG CTCACAGATG AAGTCTCCAA AATAAA    36

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( x i ) SEQUENCE DESCRIPTION: SEQ ID NO:8:

ACAGAACATT CGCTATGGCC GAGTGGAGAG ACCGCG　　　　3 6